US012604173B2

(12) United States Patent
Williams et al.

(10) Patent No.: US 12,604,173 B2
(45) Date of Patent: *Apr. 14, 2026

(54) PAIRABLE DEVICES AND SYSTEMS AND METHODS FOR PROVIDING ASSISTED PAIRING OF DEVICES TO PARTICULAR LOCATIONS

(71) Applicant: Hill-Rom Services, Inc., Batesville, IN (US)

(72) Inventors: Jason M. Williams, Cary, NC (US); Richard Schuman, Cary, NC (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/212,076

(22) Filed: May 19, 2025

(65) Prior Publication Data

US 2025/0280280 A1 Sep. 4, 2025

Related U.S. Application Data

(63) Continuation of application No. 17/551,683, filed on Dec. 15, 2021, now Pat. No. 12,342,413.
(Continued)

(51) Int. Cl.
*H04W 76/14* (2018.01)
*G16H 40/63* (2018.01)
(Continued)

(52) U.S. Cl.
CPC ............ *H04W 8/005* (2013.01); *G16H 40/63* (2018.01); *G16H 40/67* (2018.01); *H04W 76/14* (2018.02); *H04W 76/30* (2018.02)

(58) Field of Classification Search
CPC ..... H04W 8/005; H04W 76/14; H04W 76/30; H04W 12/50; H04W 4/70; H04W 48/10;
(Continued)

(56) References Cited

U.S. PATENT DOCUMENTS 7,698,156 B2 * 4/2010 Martucci ................ G16H 20/17
705/2
8,533,475 B2 9/2013 Frikart et al.
(Continued)

FOREIGN PATENT DOCUMENTS

CN 109803168 A 5/2019
EP 2020784 B1 2/2012
EP 3748646 B1 12/2020

OTHER PUBLICATIONS

European Search Report for EP Application No. 21214707.8 dated Apr. 25, 2022, 14 pages.

*Primary Examiner* — Andrew Wendell
(74) *Attorney, Agent, or Firm* — Dinsmore & Shohl LLP

(57) ABSTRACT

Systems and methods include a medical device that scans for wireless broadcasts based upon received input or satisfying a scanning criterion. The medical device, based upon the scan, identifies data wirelessly broadcast from a control device. The medical device outputs information to the interface identifying the control device. The medical device receives input from the interface selecting the control device. The medical device receives a command from the control device. The medical device physically interacts with a user based upon the command received from the control device. The medical device sends wireless confirmation of pairing to the control device. The medical device subsequently sends wireless confirmation of unpairing to the control device. The medical device performs a scan for wireless broadcasts in response to the unpairing, based upon received input or satisfying the scanning criterion.

10 Claims, 9 Drawing Sheets

Related U.S. Application Data

(60) Provisional application No. 63/127,629, filed on Dec. 18, 2020.

(51) Int. Cl.
| | |
|---|---|
| *G16H 40/67* | (2018.01) |
| *H04W 8/00* | (2009.01) |
| *H04W 76/30* | (2018.01) |

(58) Field of Classification Search
CPC ........ G16H 40/63; G16H 40/67; G16H 40/20; A61B 5/0006; A61B 5/14551; A61B 5/6833; A61B 5/742; A61B 5/01; A61B 5/02055; A61B 5/02455; A61B 5/02438; A61M 5/142
See application file for complete search history.

(56) References Cited

U.S. PATENT DOCUMENTS

| | | | |
|---|---|---|---|
| 9,596,519 B2 | 3/2017 | Endo | |
| 9,848,285 B2 | 12/2017 | Zhen et al. | |
| 10,159,465 B2 | 12/2018 | Pelissier et al. | |
| 10,290,371 B1 | 5/2019 | Pekarske et al. | |
| 10,299,307 B2 | 5/2019 | Dua | |
| 10,360,787 B2 | 7/2019 | Embree et al. | |
| 10,524,123 B2 | 12/2019 | Freeman et al. | |
| 10,616,740 B2 | 4/2020 | St. Pierre | |
| 12,039,492 B2 * | 7/2024 | Sobie | G06Q 50/22 |
| 12,342,413 B2 * | 6/2025 | Williams | H04W 8/005 |
| 2007/0168885 A1 * | 7/2007 | Muller | G06Q 10/06 707/999.003 |
| 2008/0312584 A1 | 12/2008 | Montgomery et al. | |
| 2012/0182939 A1 | 7/2012 | Rajan et al. | |
| 2014/0073252 A1 | 3/2014 | Lee et al. | |
| 2014/0180711 A1 | 6/2014 | Kamen et al. | |
| 2014/0280690 A1 * | 9/2014 | Allen | G06Q 10/1091 709/217 |
| 2015/0081335 A1 | 3/2015 | Dixon et al. | |
| 2015/0169857 A1 | 6/2015 | Wang et al. | |
| 2016/0038361 A1 | 2/2016 | Bhimavarapu et al. | |
| 2016/0283900 A1 * | 9/2016 | Johnson | G06Q 10/087 |
| 2018/0011521 A1 | 1/2018 | Ingalls et al. | |
| 2018/0110077 A1 | 4/2018 | Mandapaka et al. | |
| 2018/0189369 A1 * | 7/2018 | Baek | G06F 40/197 |
| 2018/0234900 A1 * | 8/2018 | Sankaranarayan | H04W 76/30 |
| 2018/0235016 A1 * | 8/2018 | Amschler | H04W 8/005 |
| 2018/0317826 A1 * | 11/2018 | Muhsin | G16H 10/60 |
| 2020/0213844 A1 | 7/2020 | Wang et al. | |
| 2020/0269058 A1 | 8/2020 | Mazanec et al. | |
| 2020/0389928 A1 | 12/2020 | Monson et al. | |
| 2021/0304860 A1 * | 9/2021 | Hart | G16H 50/20 |
| 2021/0337608 A1 | 10/2021 | Buil et al. | |
| 2022/0053578 A1 | 2/2022 | Schodet et al. | |

* cited by examiner

PAIRABLE DEVICES AND SYSTEMS AND METHODS FOR PROVIDING ASSISTED PAIRING OF DEVICES TO PARTICULAR LOCATIONS

CROSS-REFERENCE TO RELATED APPLICATIONS

This application is a continuation of U.S. patent application Ser. No. 17/551,683, filed Dec. 15, 2021, entitled, "PAIRABLE DEVICES AND SYSTEMS AND METHODS FOR PROVIDING ASSISTED PAIRING OF DEVICES TO PARTICULAR LOCATIONS," which claims priority to U.S. Provisional Patent Application Ser. No. 63/127,629, filed Dec. 18, 2020, entitled, "PAIRABLE DEVICES AND SYSTEMS AND METHODS FOR PROVIDING ASSISTED PAIRING OF DEVICES TO PARTICULAR LOCATIONS," the contents of which each are incorporated herein by reference in their respective entireties.

BACKGROUND

Field

The present disclosure generally relates to systems and/or methods for pairing a medical device and a control device, and more specifically, to systems and/or methods for pairing a medical device and a control device using wireless links.

Technical Background

A medical facility may include a plurality of rooms where each room may include one or more medical devices. Each medical device (MD) may be permanently fixed within a room or movable between the plurality of rooms. In addition, each medical device may be wirelessly controlled by a respective control device (CD) and the control device may be permanently fixed within a room or movable between the plurality of rooms. Accordingly, given the portable nature of medical devices and/or control devices, as well as the use of such devices with a plurality of subjects, systems and/or methods are desirable to ensure that a particular medical device is in wireless communication with a particular control device.

Wireless radios typically can transmit in excess of many meters. In a hospital environment, where there may be a wall unit or other device used to communicate with devices in a room, this could mean a plurality of devices could appear in a list of devices to pair with in a typical wireless pairing scenario, including devices in neighboring rooms or areas. A caregiver may not be able to easily select which device is in their room. For example, if a hospital bed were to be paired with the incorrect wall unit, the nurse call and bed data would be associated with the incorrect bed/occupant. This could delay care or result in improper dosage of medication (due to incorrect subject weight). Thus, the pairing process benefits from being as automated as possible and easier for the caregiver to select the proper room device.

SUMMARY

In one aspect, a pairable medical device may include a communication system configured to communicate via a communication channel, a processor, a display device configured to display an interface, and a memory storing program instructions. The program instructions, when executed by the processor, cause the processor to scan for wireless broadcasts based upon received input or satisfying a scanning criterion. The program instructions also cause the process to receive, based upon the scan, identifying data wirelessly broadcast from a control device. The program instructions further cause the processor to output information to the interface identifying the control device. The program instructions further cause the processor to receive input from the interface selecting the control device. The program instructions further cause the processor to receive a command from the control device. The program instructions further cause the processor to physically interact with a user based upon the command received from the control device. The program instructions further cause the processor to send wireless confirmation of pairing to the control device and subsequently send wireless confirmation of unpairing to the control device. The program instructions further cause the processor to perform a scan for wireless broadcasts in response to the unpairing, based upon received input or satisfying the scanning criterion.

In such an aspect, according to some aspects, the pairable medical device comprises a medical bed, a pump, a rail-mounted lift, or a computer. In an additional aspect, the scanning criterion is based upon the medical device being plugged in for power. In another aspect, the scanning criterion is based upon the medical device having brakes engaged. In yet another aspect, the pairable control device further receives identifying data wirelessly broadcast from a plurality of control devices. In a further aspect, the identifying data received from the plurality of control devices is presented on the interface according to a filtering criterion and a sorting criterion. In an additional aspect, the filtering criterion comprises a device manufacturer, a device type, or a device model. In yet another aspect, the sorting criterion comprises respective signal strengths of each wireless broadcast or location information within the identifying data.

In a further aspect, a pairable control device may comprise a communication system configured to communicate via a communication channel, a processor, and a memory storing program instructions. The program instructions, when executed by the processor, cause the processor to wirelessly broadcast self-identifying data based upon being unpaired. The program instructions further cause the processor to receive pairing confirmation from a medical device. The program instructions further cause the processor to stop the wireless broadcast in response to the received pairing confirmation. The program instructions additionally cause the processor to receive a subsequent unpairing confirmation from the medical device. The program instructions further cause the processor to resume broadcasting the self-identifying data in response to receiving the unpairing confirmation.

In such another aspect, according to some aspects, the self-identifying data comprises a first data field comprising a device name and a second data field comprises manufacturer data. In other aspects, the second manufacturer data further comprises an identifier unique to a manufacturer, followed by between 1 to 31 octets of data.

In a further aspect, a system for assisted pairing of devices may include a pairable control device that may include a first communication system configured to communicate via a communication channel, a first processor, and a memory storing first program instructions. The memory storing program instructions, when executed by the first processor, cause the first processor to wirelessly broadcast self-identifying data based upon being unpaired. The program instructions further cause the first processor to receive pairing confirmation from a medical device. The program instructions further cause the first processor to stop the wireless broadcast in response to the received pairing confirmation. The program instructions further cause the first processor to receive a subsequent unpairing confirmation from the medical device. The program instructions further cause the first processor to resume broadcasting the self-identifying data in response to receiving the unpairing confirmation. The medical device may include a display device configured to display an interface a second communication system configured to communicate via the communication channel. The medical device may be additionally configured to scan for wireless broadcasts based upon received input or satisfying a scanning criterion. The medical device may be further configured to receive, based upon the scan, identifying data wirelessly broadcast from a control device. The medical device may be further configured to output information to the interface identifying the control device. The medical device may be further configured to receive input from the interface selecting the control device. The medical device may be further configured to send wireless confirmation of pairing to the control device. The medical device may be further configured to subsequently send wireless confirmation of unpairing to the control device. The medical device may be further configured to perform a scan for wireless broadcasts in response to the unpairing, based upon received input or satisfying the scanning criterion.

In such a further aspect, according to some aspects, self-identifying data comprises a first data field comprising a device name and a second data field comprises manufacturer data comprises an identifier unique to a manufacturer, followed by between 1 to 31 octets of data. In other aspects, the scanning criterion is based upon the medical device being plugged in or the medical device having brakes engaged. Some additional aspects include receiving identifying data wirelessly broadcast from a plurality of control devices and presenting the received identifying data on the interface according to a filtering criterion and a sorting criterion. The filtering criterion may include a device manufacturer, a device type, or a device model. The sorting criterion may also include respective signal strengths of each wireless broadcast or location information within the identifying data.

In yet another aspect, a method for assisted medical device wireless pairing with a control device may include scanning, at the medical device, for wireless broadcasts based upon received input or satisfying a scanning criterion. The method may further include receiving, based upon the scan, identifying data wirelessly broadcast from the control device. The method may further include outputting, to an interface at the medical device, information identifying the control device. The method may further include receiving input from the interface selecting the control device. The method may further include sending wireless confirmation of pairing to the control device. The method may further include receiving a command from the control device. The method may further include physically interacting with a user based upon the command received from the control device. The method may further include subsequently sending wireless confirmation of unpairing to the control device. The method may further include performing an updated scan for wireless broadcasts in response to the unpairing, based upon received input or satisfying the scanning criterion.

In such still a further aspect, according to some aspects, the pairable medical device comprises a medical bed, a pump, a rail-mounted lift, or a computer. In another such aspect, the scanning criterion may be based upon the medical device being plugged in. In other such aspects, the scanning criterion may be based upon the medical device having brakes engaged. Still other such aspects may include receiving identifying data wirelessly broadcast from a plurality of control devices. In other such aspects, the identifying data received from the plurality of control devices may be presented on the interface according to a filtering criterion and a sorting criterion. Additional such aspects may include a filtering criterion comprising a device manufacturer, a device type, or a device model. In other such aspects, the sorting criterion may comprise respective signal strengths of each wireless broadcast or location information within the identifying data.

In still a further aspect, a method for assisted control device wireless pairing with a medical device may include wirelessly broadcasting self-identifying data from the control device based upon being unpaired. The method may further include receiving pairing confirmation from the medical device. The method may further include stopping the wireless broadcast in response to the received pairing confirmation. The method may further include receiving a subsequent unpairing confirmation from the medical device. The method may further include resuming broadcasting of the self-identifying data in response to receiving the unpairing confirmation.

In such still a further aspect, according to some aspects, the self-identifying data may comprise a first data field comprising a device name and a second data field comprises manufacturer data. Still other such aspects may include the second manufacturer data further comprising an identifier unique to a manufacturer, followed by between 1 to 31 octets of data.

In still a further aspect, a method for assisted wireless pairing of a medical device and a control device may include wirelessly broadcasting, from the control device, self-identifying data based upon being unpaired. The method may further include scanning, at the medical device, for wireless broadcasts based upon received input or satisfying a scanning criterion. The method may further include receiving at the medical device, based upon the scan, identifying data wirelessly broadcast from the control device. The method may further include outputting, from the medical device to the interface, information identifying the control device. The method may further include receiving input from the interface selecting the control device. The method may further include sending wireless confirmation of pairing from the medical device to the control device. The method may further include receiving, at the control device, pairing confirmation from the medical device. The method may further include stopping the wireless broadcast from the control device in response to the received pairing confirmation. The method may further include subsequently sending wireless confirmation of unpairing from the medical device to the control device. The method may further include receiving at the control device a subsequent unpairing confirmation from the medical device. The method may further include resuming broadcasting of the self-identifying data at the control device in response to receiving the unpairing confirmation from the medical device. The method may further include performing an updated scan for wireless broadcasts at the medical device in response to the unpairing, based upon received input or satisfying the scanning criterion.

In such yet a further aspect, according to some aspects, the self-identifying data may include a first data field comprising a device name and a second data field comprises manufacturer data comprises an identifier unique to a manufacturer, followed by between 1 to 31 octets of data. The scanning criterion may be based upon the medical device being plugged in or the medical device having brakes engaged. The method may further include receiving identifying data wirelessly broadcast from a plurality of control devices and presenting the received identifying data on the interface according to a filtering criterion and a sorting criterion. In other such aspects, the filtering criterion may include a device manufacturer, a device type, or a device model. In yet another aspect, the sorting criterion may include respective signal strengths of each wireless broadcast or location information within the identifying data.

Additional features and advantages of the embodiments described herein will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Figure 1A:
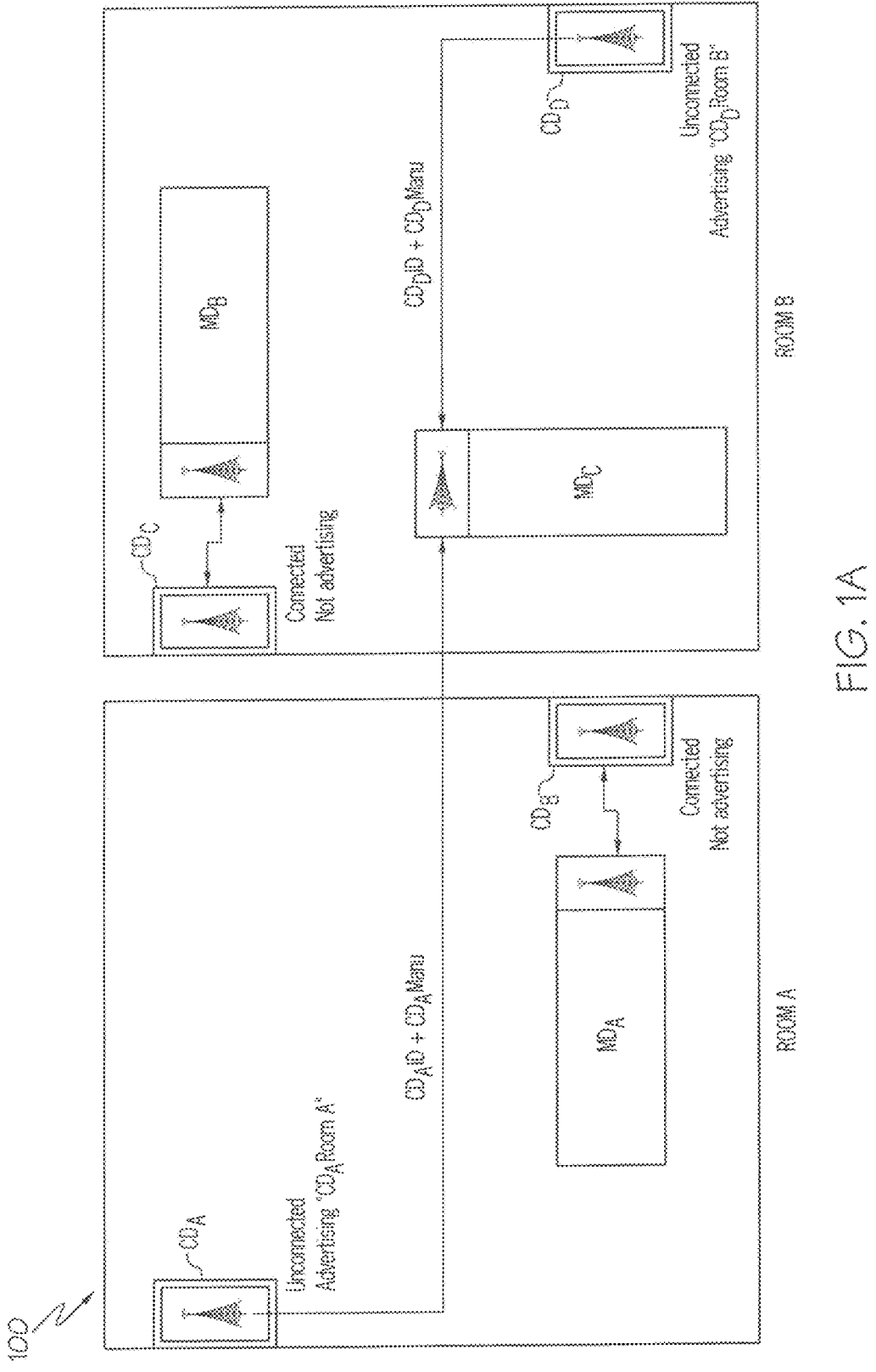
FIG. 1A depicts a block diagram illustrating control devices wirelessly advertising to a medical device and a plurality of medical devices wirelessly paired to other control devices that are distributed amongst a plurality of rooms of a medical facility, according to one or more embodiments shown and described herein.

Reference will now be made in detail to embodiments to pair a medical device and a control device using wireless radio frequency, examples of which are illustrated in the accompanying drawings. Whenever possible, the same reference numerals will be used throughout the drawings to refer to the same or like parts. Various embodiments of the present disclosure are depicted in FIG. 1A. In general, a medical facility 100 may include a plurality of rooms and/or a plurality of floors (e.g., Rooms A and B on one floor, other rooms may be on other floors). In such aspects, one or more medical devices (e.g. $MD_A$, $MD_B$, and/or $MD_C$) and one or more control devices ($CD_A$, $CD_B$, $CD_C$, and/or $CD_D$), may be distributed amongst the rooms, floors (see FIGS. 1A-1B), and/or within sub-spaces within a given room (e.g., a large triage room with multiple beds, hospital rooms that are shared by 2 or more subjects, etc.).

In one aspect, referring to FIG. 1A, a control device (e.g., $CD_D$) and a medical device (e.g., $MD_C$) may be fixedly positioned within a room (e.g., Room B). A control device CD may be any device capable of pairing/unpairing (also referred to herein as connecting/disconnecting) with a medical device, and sending commands to control a medical device. By way of non-limiting example, a control device may be any device capable of wirelessly pairing with a medical device and issuing commands to the medical device, such as a tethered hand control unit, a wireless hand control unit, a wall mounted control unit, any type of computer (tablet, smartphone, laptop, desktop, etc.), and the like. A medical device may any medical device capable of wirelessly pairing/unpairing with a control device, and implementing commands received from a control device. By way of non-limiting example, a medical device may be a medical bed, a pump, a rail-mounted lift, a computer, and the like. In this aspect, a control device ($CD_A$, $CD_B$, $CD_C$, $CD_D$, and/or the like) may be permanently located in a particular location, such as room A or room B. When unpaired, a control device may broadcast data having multiple fields, such as a device name field. A device name field (hereinafter also referred to as an identifier) may be any suitable text, such as a location descriptor ("Control Device A Room A East") that would typically be human-readable and descriptive of its location. In some aspects, a control device may be relocated to another location and/or have its device name field updated accordingly. A manufacturer-specific data field may include customized data used in the advertising of packets as part of the data broadcast. In aspects, some utilizing Bluetooth for wireless communications, the manufacturer-specific data field may include a company identifier, brand identifier, model identifier, device-type identifier, and the like. In some aspects, this may be followed by additional data, such as 31 octets of data, although any suitable amount/type of data may be utilized in other aspects. Any suitable wireless protocol may be utilized, such as Bluetooth, BLE, Zigbee, Z-Wave, 6LoWPAN, Thread, and the like.

In some aspects, control devices ($CD_A$, $CD_B$, $CD_C$, $CD_D$, and/or the like) may wirelessly transmit (e.g., via a Bluetooth RF signal and/or radio frequency identification (RFID)) their identifiers ($CD_A$ID, $CD_B$ID, $CD_C$ID, $CD_D$ID, and/or the like) and/or manufacturer-specific data fields ($CD_A$Manu, $CD_B$Manu, $CD_C$Manu, $CD_D$Manu, and/or the like) to medical devices ($MD_A$, $MD_B$, $MD_C$, and/or the like). Since a wireless signal may penetrate the walls and/or floors of the medical facility 100, a number of medical devices within range (e.g., up to 300 feet for Class 1. Bluetooth, up to 33 feet for Class 2. Bluetooth, and/or the like) may wirelessly receive the control device identifiers ($CD_A$ID, $CD_B$ID, $CD_C$ID, and/or the like). Another control device $CD_A$ resides in a different room, namely room A. Both $CD_A$ and $CD_D$ are broadcasting data, which include the respective device name fields ($CD_A$ID and $CD_D$ID) and the respective manufacturer-specific data fields ($CD_A$Manu and $CD_D$Manu). By contrast, other control devices are paired with medical devices, and therefore not broadcasting data. Within room A, medical device $MD_A$ is paired with control device $CD_B$. Similarly, within room B, medical device $MD_B$ is paired with control device $CD_C$. Paired control devices $CD_B$ and $CD_C$ are not broadcasting data in this aspect because, once paired, control devices may not broadcast data again until unpaired. In other aspects, control devices may continue broadcasting data to other medical devices during pairing. Each medical device (e.g., $MD_C$) may be configured to scan its wireless communication channel (e.g., Bluetooth channel). Medical device $MD_C$ scans the identifiers and manufacturer-specific data received from control devices $CD_A$ and $CD_D$. A medical device in this aspect may not continue to scan once paired to a control device. In other aspects a medical device may continue to scan while paired to a control device.

Figure 1B:
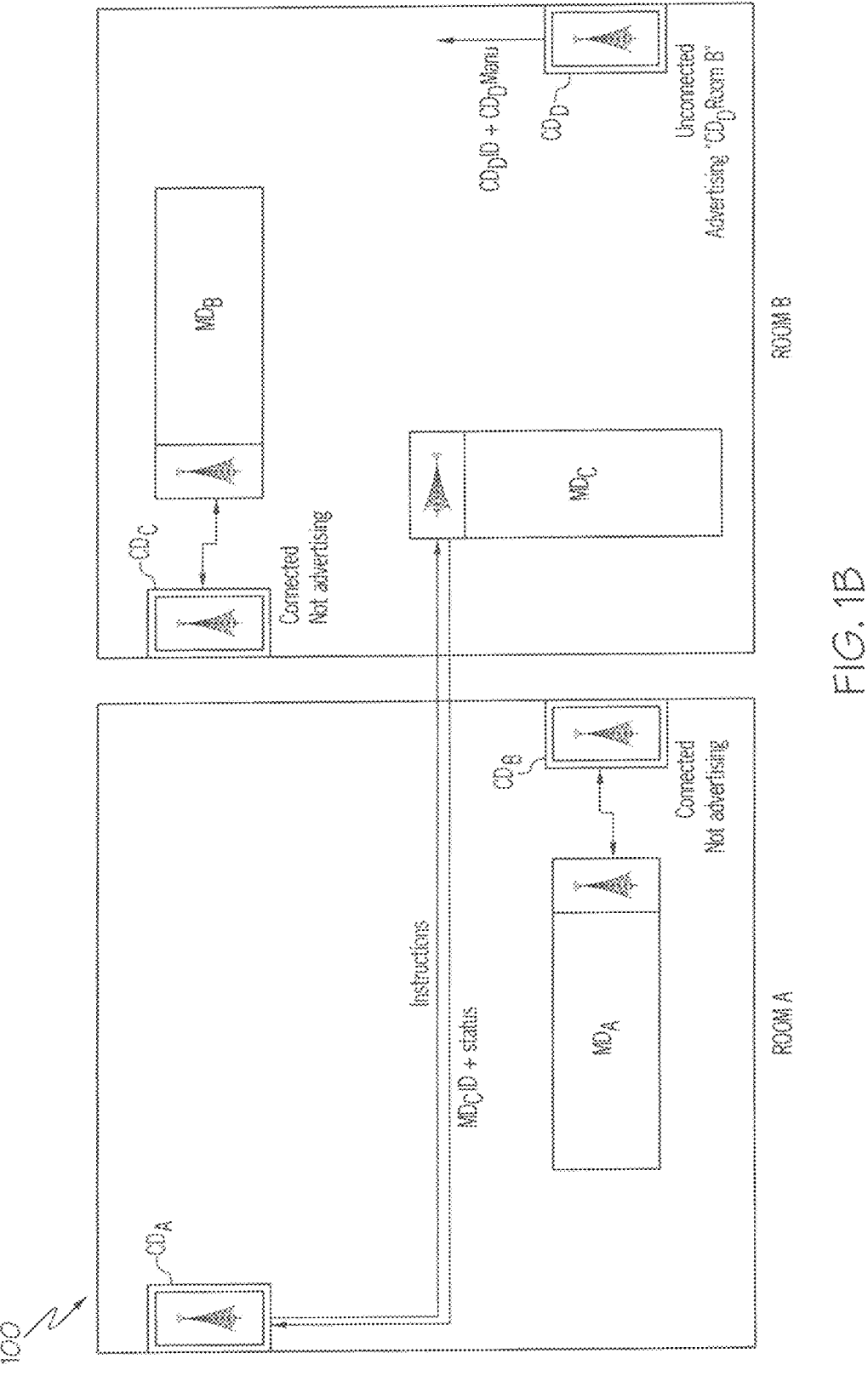
FIG. 1B depicts a block diagram illustrating a control device wirelessly advertising to medical devices and a plurality of medical devices wirelessly paired to other control devices that are distributed amongst the plurality of rooms of the medical facility, according to one or more embodiments shown and described herein.

Continuing with the same aspect, FIG. 1B depicts a block diagram illustrating control devices wirelessly advertising to a medical device and a plurality of medical devices wirelessly paired to other control devices that are distributed amongst the plurality of rooms of the medical facility. In some aspects, a control device $CD_A$ may pair with a medical device $MD_C$ such that the medical device $MD_C$ pairs to the identified control device $CD_A$. Once paired, the control device $CD_A$ may transmit control signals to the medical device $MD_C$ and the medical device $MD_C$ may begin to receive control signals (also known as instructions herein) from the control device $CD_A$. Additionally, the medical device $MD_C$ may transmit status updates to the control device $CD_A$ and the medical device $MD_C$ may receive status updates from the control device $CD_A$. Since the medical device $MD_C$ is now paired, control device $CD_A$ is no longer broadcasting data. By contrast, control device $CD_D$ is still not paired and thus continues broadcasting data. In another aspect, if the medical device $MD_C$ stops receiving instructions (or any other data in some aspects) from control device $CD_A$, medical device $MD_C$ may be configured to automatically disassociate from control device $CD_C$ over their respective wireless communication channels and/or vice versa if the control device $CD_C$ no longer receives any data from the medical device $MD_C$. As discussed herein, a medical device and/or control device may provide an indicator (visual, audio, and the like) of pairing and/or unpairing.

Figure 1C:
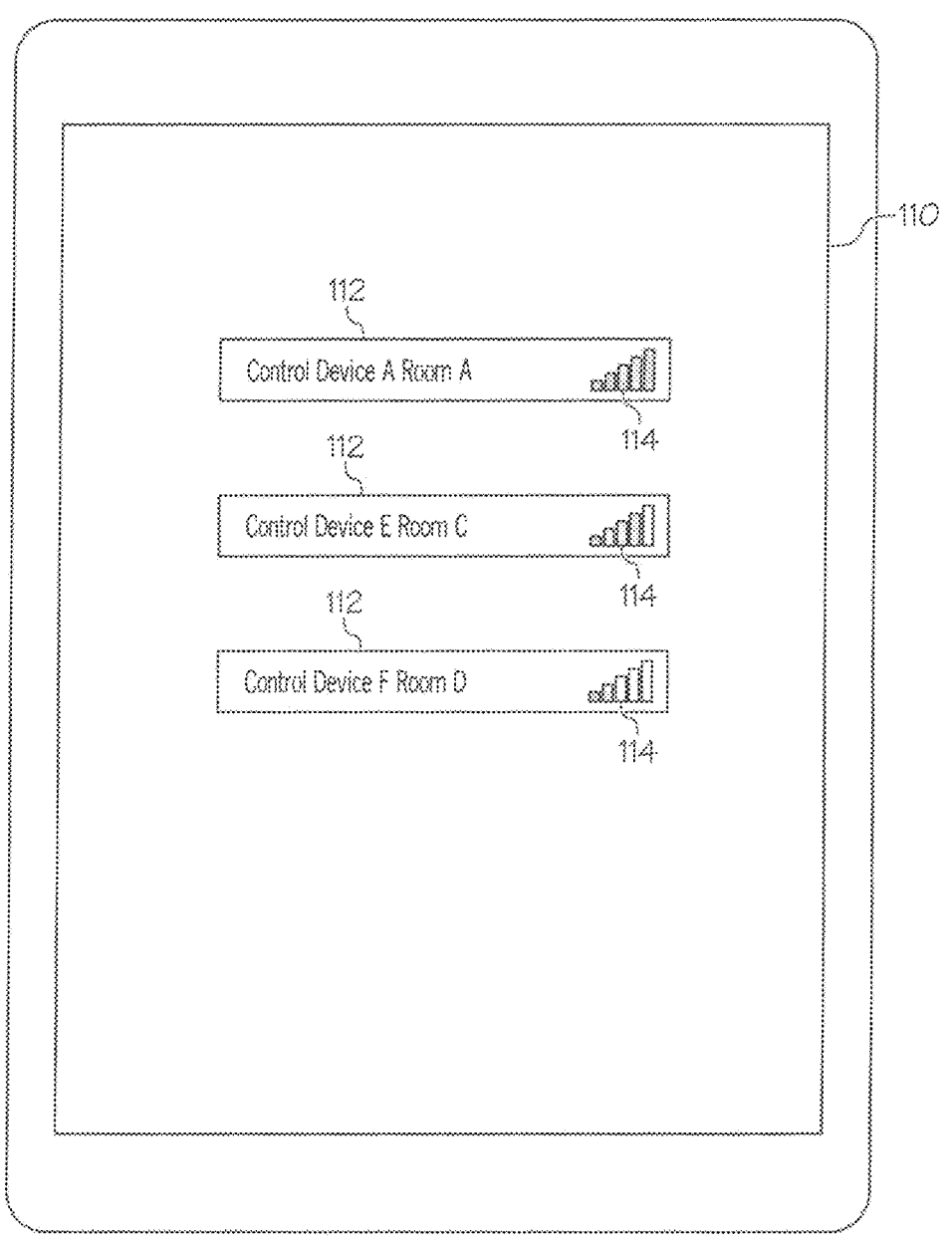
FIG. 1C depicts an exemplary medical device graphical interface illustrating a plurality of wireless control devices selectable according to signal strength and/or room location within the medical facility, according to one or more embodiments shown and described herein.

Continuing with the aspect of FIGS. 1A-1B, FIG. 1C depicts an exemplary medical device graphical interface 110 illustrating a plurality of wireless control devices selectable according to signal strength 114 and/or room location within the medical facility. The medical device graphical interface 110 in this aspect is presented on a touch display located on a medical device, although any suitable device capable of displaying a graphical interface 110 may be utilized. Here, the medical device is scanning for data broadcast from control devices after having been wheeled into room A. As discussed herein, medical device actions such as applying the brakes or being plugged into the wall for power may initiate the medical device to begin scanning. As shown in the medical device graphical interface 110, three control devices are presented as selectable options. Each medical device may be presented with its device name field 112, which in this aspect may include the room number in the device name. In some aspects, the device name field 112 may be updated by any appropriate user or administrator. In other aspects, any other suitable identifying information may be included (floor, building, control device type, and the like) in the device name field 112. Other types of data fields may be utilized for display such as room number, floor number, building, and the like, by which control devices may be sorted and/or filtered. Control devices may be filtered by any suitable criteria, such as manufacturer or control device type, which may be contained in the manufacturer-specific data field. In this aspect, control devices from other manufacturers are not displayed even if they are broadcasting data. This can help ensure compatibility and the integrity of communications between the medical device and any control devices satisfying the filtering criteria. Among control devices that meet the filtering criteria, such as being from a specified manufacturer, control device options may be sorted by any suitable criteria. In this aspect, control devices $CD_A$, $CD_E$, $CD_F$, are sorted by their respective Bluetooth signal strengths 114, although any quantity and/or type of sorting criteria may be utilized, such as room number, floor number, manufacturer, and the like.

Figure 2A:
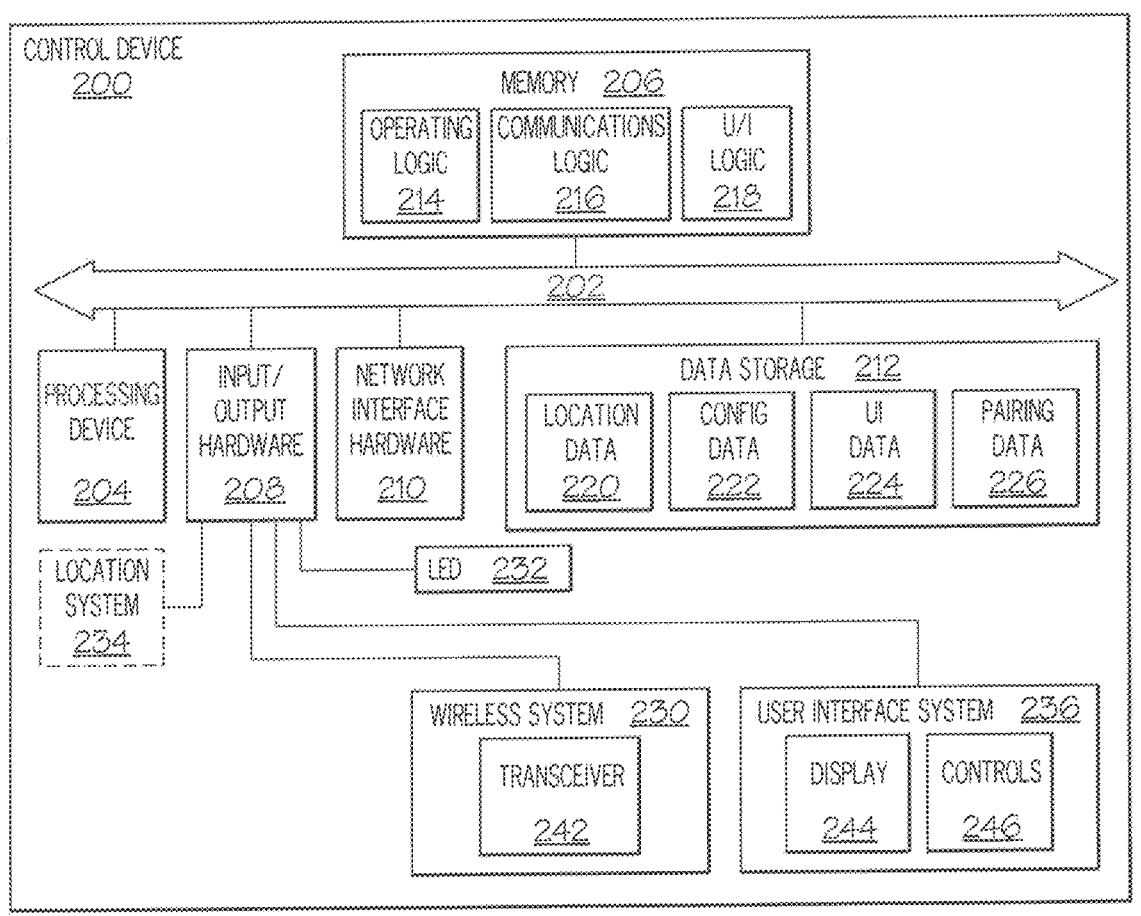
FIG. 2A depicts illustrative internal components of a control device that are communicatively coupled to one another to provide wireless identification and pairing to a medical device and wireless control of the medical device, according to one or more embodiments shown and described herein.

FIG. 2A depicts illustrative internal components of a control device 200 that are communicatively coupled to one another to provide wireless link pairing with and control of a medical device, according to one or more embodiments of the present disclosure. As shown in FIG. 2A, the control device 200 may include a local interface 202 (e.g., a bus) that communicatively interconnects the various components, including, but not limited to, a processing device 204, memory 206, input/output hardware 208, network interface hardware 210, and/or a data storage device 212.

The processing device 204, such as a computer processing unit (CPU), may be the central processing unit of the control device 200, performing calculations and logic operations required to execute a program. The processing device 204, alone or in conjunction with one or more of the other elements disclosed in FIG. 2A, is an illustrative processing device, computing device, processor, or combination thereof, as such terms are used in this disclosure.

The memory 206, such as read only memory (ROM) and random access memory (RAM), may constitute illustrative memory devices (i.e., non-transitory, processor-readable storage media). Such memory 206 may include one or more programming instructions thereon that, when executed by the processing device 204, cause the processing device 204 to complete various processes, such as the processes described herein. Optionally, the program instructions may be stored on a tangible computer-readable medium such as a digital disk, flash memory, a memory card, a USB drive, an optical disc storage medium (e.g., Blu-ray™, CD, DVD), and/or other non-transitory processor-readable storage media.

In some embodiments, the program instructions contained on the memory 206 may be embodied as a plurality of software modules, where each module provides programming instructions for completing one or more tasks. For example, as shown in FIG. 2A, the memory 206 may contain one or more of operating logic 214, communications logic 216, and UI logic 218. It should be understood that the various logic modules described herein with respect to FIG. 2A are merely illustrative, and that other logic modules, including logic modules that combine the functionality of two or more of the modules described hereinabove, may be used without departing from the scope of the present disclosure.

Still referring to FIG. 2A, the data storage device 212, which may generally be a storage medium that is separate from the memory 206, may contain a data repository for storing electronic data and/or the like relating to the location of the control device 200, an identification of the control device 200, configuration settings, UI data, and/or the like. The data storage device 212 may be any physical storage medium, including, but not limited to, a hard disk drive (HDD), memory, removable storage, and/or the like. While the data storage device 212 is depicted as a local device, it should be understood that the data storage device 212 may be a remote storage device that is remotely located from the control device 200, such as, for example, a server computing device or the like. Illustrative data that may be contained within the data storage device 212 may include, for example, location data 220, configuration data 222, UI data 224, pairing data 226, and/or the like. Pairing data 226 may include identification data (serial number, etc.) one or more medical device identifiers to which the control device 200 is or has been paired via the methods as described herein.

The input/output hardware 208 may generally include a wireless system 230, an indicator 232, a location system 234, and a user interface system 236. The wireless system 230 may include a transceiver 242 configured to transmit and to receive wireless signals (e.g., RF, Bluetooth, UWB, and/or the like) according to the respective wireless protocols. In some aspects, data transmission techniques including encryption/decryption, forward error correction, and/or the like may be instituted. The indicator 232 may include a light emitting diode, indicator light, and/or the like. The location system 234 may include a Global Positioning System (GPS), a Global Navigation Satellite System (GLONASS), a Wi-Fi locating system, and/or the like. The user interface system 236 may include a display 244 and/or user interface controls 246 configured to receive control inputs for transmission via the input/output hardware 208 and to display outputs received from the input/output hardware 208.

The network interface hardware 210 may generally provide the control device 200 with an ability to interface with one or more external devices, such as, for example, a medical facility server, a nurse station, and/or the like. Communication with external devices may occur using various communication ports (not shown). An illustrative communication port may be attached to a communications network, such as the Internet, an intranet, a local network, a direct connection, and/or the like.

It should be understood that in some embodiments, the input/output hardware 208 and the network interface hardware 210 may be combined into a single device that allows for communications with other devices, regardless of whether such other devices are located within the control device 200.

It should be understood that the components illustrated in FIG. 2A are merely illustrative and are not intended to limit the scope of the present disclosure. More specifically, while the components in FIG. 2A are illustrated as residing within the control device, this is a non-limiting example. In some embodiments, one or more of the components may reside external to the control device. Similarly, one or more of the components may be embodied in other devices not specifically described herein. Furthermore, various control devices are described herein (e.g., FIG. 3) and are non-limiting examples. Other control devices may include a user's personal cell-phone, a nurse's call system device, and/or the like with wireless communication channel capabilities.

Figure 2B:
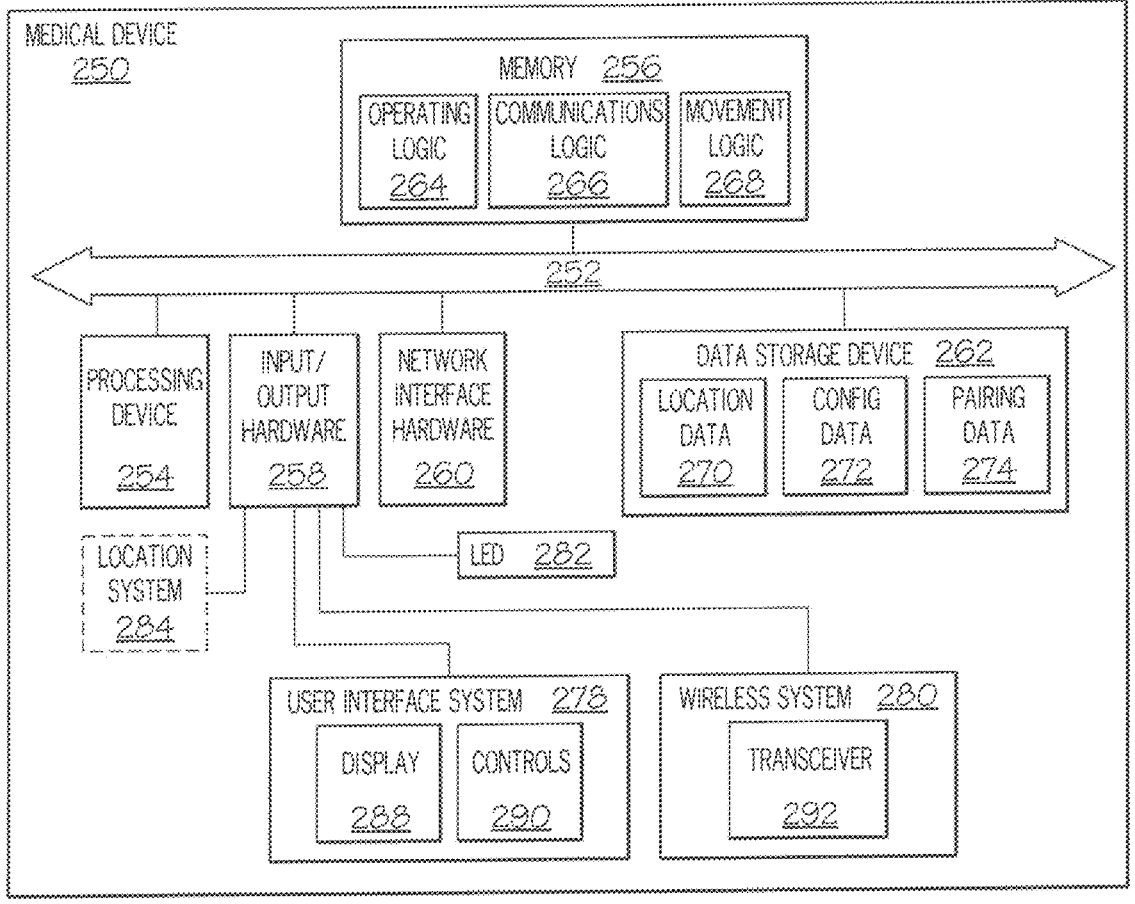
FIG. 2B depicts illustrative internal components of a medical device that are communicatively coupled to one another, receive identification from a control device, and receive wireless control from a control device, according to one or more embodiments shown and described herein.

FIG. 2B depicts illustrative internal components of a medical device 250 that are communicatively coupled to one another to provide wireless link pairing with a control device, according to one or more embodiments of the present disclosure. As shown in FIG. 2B, the medical device 250 may include a local interface 252 (e.g., a bus) that communicatively interconnects the various components, including, but not limited to, a processing device 254, memory 256, input/output hardware 258, network interface hardware 260, and/or a data storage device 262.

The processing device 254, such as a computer processing unit (CPU), may be the central processing unit of the medical device 250, performing calculations and logic operations required to execute a program. The processing device 254, alone or in conjunction with one or more of the other elements disclosed in FIG. 2B, is an illustrative processing device, computing device, processor, or combination thereof, as such terms are used in this disclosure.

The memory 256, such as read only memory (ROM) and random access memory (RAM), may constitute illustrative memory devices (i.e., non-transitory, processor-readable storage media). Such memory 256 may include one or more programming instructions thereon that, when executed by the processing device 254, cause the processing device 254 to complete various processes, such as the processes described herein. Optionally, the program instructions may be stored on a tangible computer-readable medium such as a digital disk, flash memory, a memory card, a USB drive, an optical disc storage medium (e.g., Blu-ray™, CD, DVD), and/or other non-transitory processor-readable storage media.

In some embodiments, the program instructions contained on the memory 256 may be embodied as a plurality of software modules, where each module provides programming instructions for completing one or more tasks. For example, as shown in FIG. 2B, the memory 256 may contain one or more of operating logic 264, communications logic 266, and movement logic 268. It should be understood that the various logic modules described herein with respect to FIG. 2B are merely illustrative, and that other logic modules, including logic modules that combine the functionality of two or more of the modules described hereinabove, may be used without departing from the scope of the present disclosure.

Still referring to FIG. 2B, the data storage device 262, which may generally be a storage medium that is separate from the memory 256, may contain a data repository for storing electronic data and/or the like relating to the location of the medical device 250, an identification of the medical device 250, configuration settings, and/or the like. The data storage device 262 may be any physical storage medium, including, but not limited to, a hard disk drive (HDD), memory, removable storage, and/or the like. While the data storage device 262 is depicted as a local device, it should be understood that the data storage device 262 may be a remote storage device that is remotely located from the medical device 250, such as, for example, a server computing device or the like.

Illustrative data that may be contained within the data storage device 262 may include, for example, location data 270, configuration data 272, pairing data 274, and/or the like. Pairing data 274 may include one or more control device identifiers to which the medical device 250 is or has been paired via the methods as described herein.

The input/output hardware 258 may generally include a user interface system 278, a wireless system 280, an indicator 282, and a location system 284. The user interface system 278 may include a display 288 and/or user interface controls 290 configured to receive control inputs for transmission via the input/output hardware 258 and to display outputs received from the input/output hardware 258. The wireless system 280 may include a transceiver 292 configured to transmit and to receive wireless signals (e.g., RFID, RF, Bluetooth, UWB, and/or the like) according to the respective wireless protocols. In some aspects, data transmission techniques including encryption/decryption, forward error correction, and/or the like may be instituted. The indicator 282 may include a light emitting diode, indicator light, and/or the like. The location system 284 may include a Global Positioning System (GPS), a Global Navigation Satellite System (GLONASS), a Wi-Fi locating system, and/or the like.

The network interface hardware 260 may generally provide the medical device 250 with an ability to interface with one or more external components, such as, for example, a medical facility server, a nurse station, and/or the like. Communication with external devices may occur using various communication ports (not shown). An illustrative communication port may be attached to a communications network, such as the Internet, an intranet, a local network, a direct connection, and/or the like.

It should be understood that in some embodiments, the input/output hardware 258 and the network interface hardware 260 may be combined into a single device that allows for communications with other devices, regardless of whether such other devices are located within the medical device 250.

It should be understood that the components illustrated in FIG. 2B are merely illustrative and are not intended to limit the scope of this disclosure. More specifically, while the components in FIG. 2B are illustrated as residing within the medical device 250, this is a non-limiting example. In some embodiments, one or more of the components may reside external to the medical device 250. Similarly, one or more of the components may be embodied in other devices not specifically described herein.

Figure 3:
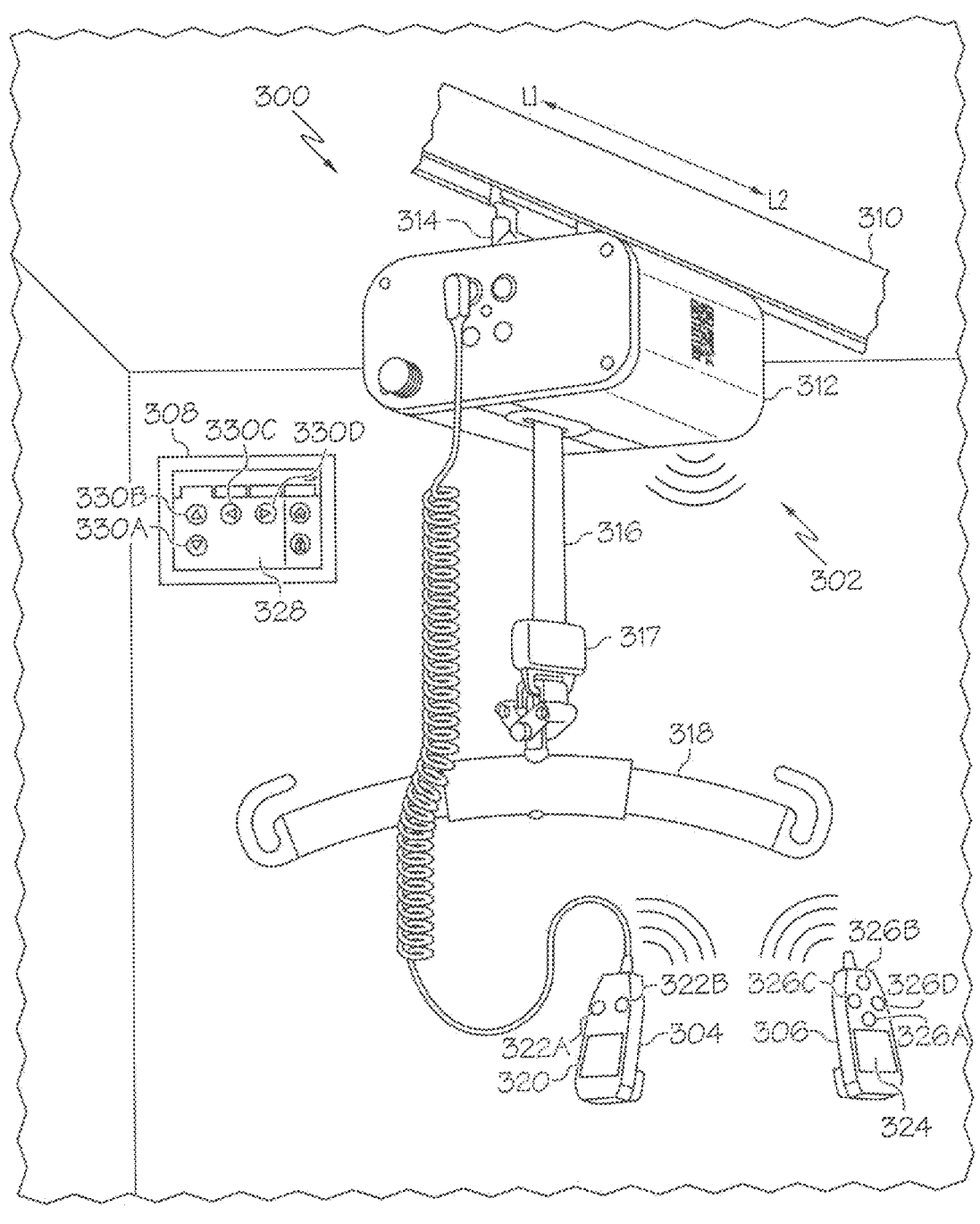
FIG. 3 depicts an illustrative wireless link pairing system including a rail-mounted lift as a medical device, and a tethered hand control unit, a wireless hand control unit, and/or a wall-mounted control unit as control devices, according to one or more embodiments shown and described herein.

FIG. 3 depicts one illustrative wireless link pairing system 300 including a rail-mounted lift 302 as an illustrative medical device and a plurality of remote devices 304, 306, 308, as control devices, according to one or more embodiments of the present disclosure. Referring to FIG. 3, the rail-mounted lift 302 is coupled to a rail 310. According to various aspects, the rail 310 may extend along a ceiling of a room (e.g., Room A of FIG. 1), along a ceiling of more than one room (e.g., Room A and Room B of FIG. 1), and/or the like. More specifically, the rail-mounted lift 302 includes a lift unit 312 that is slidably coupled to the rail 310 via a carriage 314. The lift unit 312 may be used to support and/or lift a subject with a lifting strap 316 which is coupled to a motor (not shown) contained within the lift unit 312. The motor facilitates extending or retracting the lifting strap 316 from the lift unit 312, thereby raising and lowering a subject attached to the lifting strap 316. According to various embodiments, a subject may be attached to the lifting strap 316 with a sling bar 318 or a similar accessory attached to the lifting strap 316 via a coupling 317. The sling bar 318 or a similar accessory may be attached to a harness or a sling in which the subject is positioned, thereby facilitating the lifting operation.

Various components of the rail-mounted lift 302, such as the lift unit 312 and/or components thereof, may be operated with a tethered hand control unit 304, a wireless hand control unit 306 and/or a wall-mounted control unit 308 communicatively couplable to the lift unit 312. In view of FIG. 3, the tethered hand control unit 304 may be directly wired to the lift unit 312 and/or wirelessly coupled or paired to the lift unit 312 (e.g., according to the methods described herein) to facilitate remote operation of the rail-mounted lift 302. According to various aspects, the tethered hand control unit 304 may include a display 320 and one or more user interface controls 322A (e.g., to extend lifting strap 316), 322B (e.g., to retract lifting strap 316). Similarly, the wireless hand control unit 306 may be wirelessly coupled or paired to the lift unit 312 (e.g., according to the methods described herein) and may include a display 324 and one or more user interface controls 326A (e.g., to extend lifting strap 316), 326B (e.g., to retract lifting strap), 326C (e.g., to translate lift unit 312 in a first lateral direction L1 along rail 310), 326D (e.g., to translate lift unit 312 in a second lateral direction L2 along rail 310), and the wall-mounted control unit 308 may be wirelessly coupled or paired to the lift unit 312 (e.g., according to the methods described herein) and may include a display 328 and one or more user interface controls 330A (e.g., to extend lifting strap 316), 330B (e.g., to retract lifting strap 316), 330C (e.g., to translate lift unit 312 in a first lateral direction L1 along rail 310), 330D (e.g., to translate lift unit 312 in a second lateral direction L2 along rail 310). Further user interface controls of the wall-mounted control unit 308 may activate the lift unit 312, pair a subject with the lift unit 312, return the lift unit 312 to a "home" position/location, receive information from the lift unit 312 (e.g., battery status, magnitude of load supported by the lift unit, and/or the like), actuate an emergency stop of the lift unit 312, reset the lift unit 312, and/or the like.

Figure 4A:
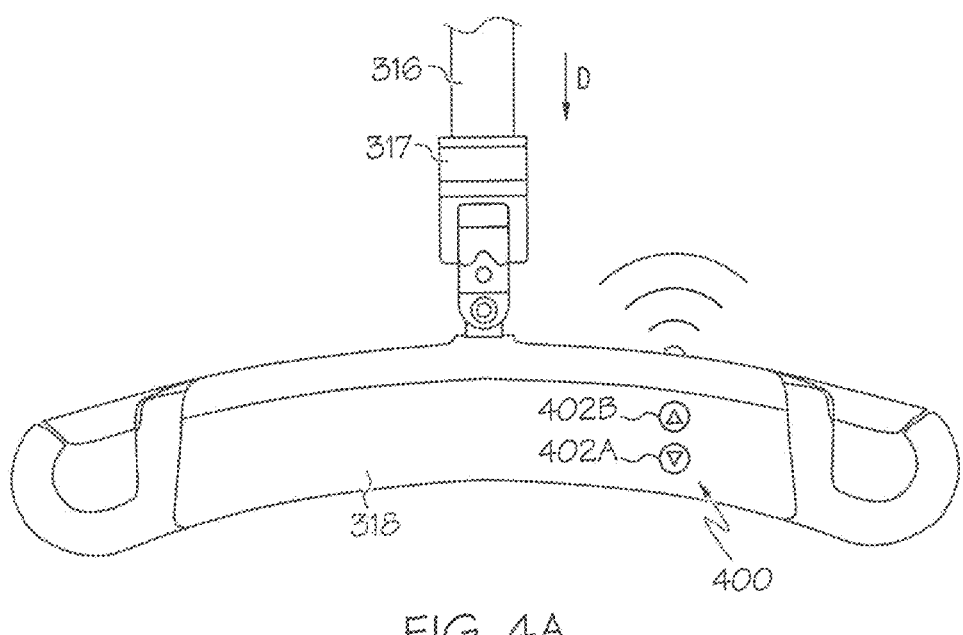
FIG. 4A depicts an illustrative sling bar control unit as a control device, according to one or more embodiments shown and described herein.
Figure 4B:
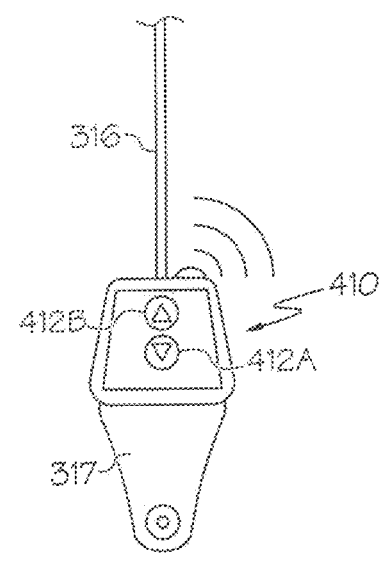
FIG. 4B depicts an illustrative coupling control unit as a control device, according to one or more embodiments shown and described herein.

Referring to FIGS. 4A and 4B, according to further aspects of the present disclosure, the rail-mounted lift 302 (e.g., FIG. 3) may be operated with a sling bar control unit 400 positioned on the sling bar 318 and/or a coupling control unit 410 positioned on the coupling 317 attached to a distal "D" end of the lifting strap 316. The sling bar control unit 400 may be wirelessly coupled or paired to the lift unit 312 (e.g., according to the methods described herein) and may include one or more user interface controls 402A (e.g., to extend lifting strap 316), 402B (e.g., to retract lifting strap 316). Similarly, the coupling control unit 410 may be wirelessly coupled or paired to the lift unit 312 (e.g., according to the methods described herein) and may include one or more user interface controls 412A (e.g., to extend lifting strap 316), 412B (e.g., to retract lifting strap 316).

In light of FIGS. 3, 4A and 4B, a plurality of control devices (e.g., a tethered hand control unit 304, a wireless hand control unit 306, a wall-mounted control unit 308, a sling bar control unit 400, a coupling control unit 410, and/or
the like) may already be physically present in a room in the
aspect. In other aspects, control devices may be physically
brought into the room, and/or physically taken out of the
room. According to some aspects of the present disclosure,
a medical device (e.g., the rail-mounted lift 302) may be
fixedly positioned within a room. In such aspects, referring
to FIGS. 3 and 4B, control devices that physically remain in
that room (e.g., wall-mounted control unit 308) and physi-
cally remain coupled to the medical device itself in that
room (e.g., tethered hand control unit 304, coupling control
unit 410), remain wirelessly connected to the medical
device, and the medical device may be configured to remain
paired with one or more of such control devices. For
example, the rail-mounted lift 302 may store pairing data
(FIG. 2B, reference 274, e.g., associated CD IDs in a fixed
pairings file), in its data storage device (FIG. 2B, reference
262) for each control device that physically remains in its
room and/or physically remains coupled to the rail-mounted
lift 302. Further in such aspects, referring to FIGS. 3 and 4A,
one or more control devices may not physically remain in
that room (e.g., wireless hand control unit 306, sling bar
control unit 400). In such aspects, the medical device may be
configured to not only pair with such control devices as they
are brought into a room but also periodically or continually
monitor pairings with such control devices. Periodically, as
described herein, may refer to a regularly occurring interval
or time period (e.g., every "X" seconds, every "Y" minutes,
and/or the like). Continuing the example, the rail-mounted
lift 302 may store pairing data (e.g., FIG. 2B, reference 274,
e.g., associated CD IDs in a transient pairings file), in its data
storage device (e.g., FIG. 2B, reference 262) for each control
device that may not physically remain in its room and the
rail-mounted lift 302 may periodically determine whether
each control device identifier (e.g., CD ID) is still being
received over its wireless communication channel. Accord-
ing to various aspects, if control device input (e.g., stored in
a transient pairings file) is still being wirelessly received, the
medical device (e.g., rail-mounted lift) may remain paired
with that control device and if the paired control device
identifier is not still being wirelessly received, the medical
device may automatically disassociate from that control
device (e.g., the medical device considered as physically
taken out of the room).

According to other aspects of the present disclosure, a
medical device (e.g., a rail-mounted lift 302) may not be
fixedly positioned within a room. For example, a lift unit
may be moved along a rail 310 (FIG. 3) from one room (e.g.,
FIG. 1, Room A) to another room (e.g., FIG. 1, Room B). In
such aspects, referring to FIGS. 3 and 4B, control devices
that physically remain coupled to the medical device itself
(e.g., tethered hand control unit 304, coupling control unit
410), remain wirelessly connected to the medical device and
the medical device may be configured to remain paired with
all such control devices. For example, the rail-mounted lift
302 may store pairing data (FIG. 2B, reference 274, e.g.,
associated CD IDs in a fixed pairings file), in its data storage
device (FIG. 2B, reference 262) for each control devices that
physically remains coupled to the rail-mounted lift 302.
Further in such aspects, referring to FIGS. 3 and 4A, one or
more control devices may not be physically coupled to the
medical device itself. This may include control devices that
physically remain in a given room (e.g., wall-mounted
control units 308) and/or control devices that may not
physically remain in any given room (e.g., wireless hand
control unit 306, sling bar control unit 400). In such aspects,
the medical device may be configured to not only pair with such control devices but also periodically or continually
monitor pairings with such control devices. Continuing the
example, the rail-mounted lift 302 may store pairing data
(e.g., FIG. 2B, reference 274, e.g., associated CD IDs in a
transient pairings file), in its data storage device (e.g., FIG.
2B, reference 262) for each control device that physically
remains in a given room and that may not physically remain
in any given room and the rail-mounted lift 302 may
periodically determine whether each control device identi-
fier (e.g., CD ID) is still communicating with the rail-
mounted lift 302 over its wireless communication channel.

According to various aspects, upon detecting movement
(e.g., translation along rail 310) the medical device may be
configured to continually monitor pairings with such control
devices. Accordingly, if a control device identifier (e.g., CD
ID of a wireless hand control unit 306 being used to translate
or move the rail-mounted lift 302 between rooms, CD ID of
a sling bar control unit 400 being moved with the rail-
mounted lift 302 between rooms) or other data is still being
wirelessly received, the medical device (e.g., rail-mounted
lift) may remain paired with the control device(s) and if the
control device identifier (e.g., CD ID of a wall-mounted
control unit 308 in a former room, CD ID of a sling bar
control unit 400 not moved to a new room) or other data
from the control device is not still being wirelessly received,
the medical device may automatically disassociate from any
such control device(s). Further in such an aspect, the medi-
cal device may be configured to provide on its graphical
interface 110 for pairing new control devices (e.g., wall-
mounted control unit 308 in new room) as the medical
device transitions between rooms.

Figure 5:
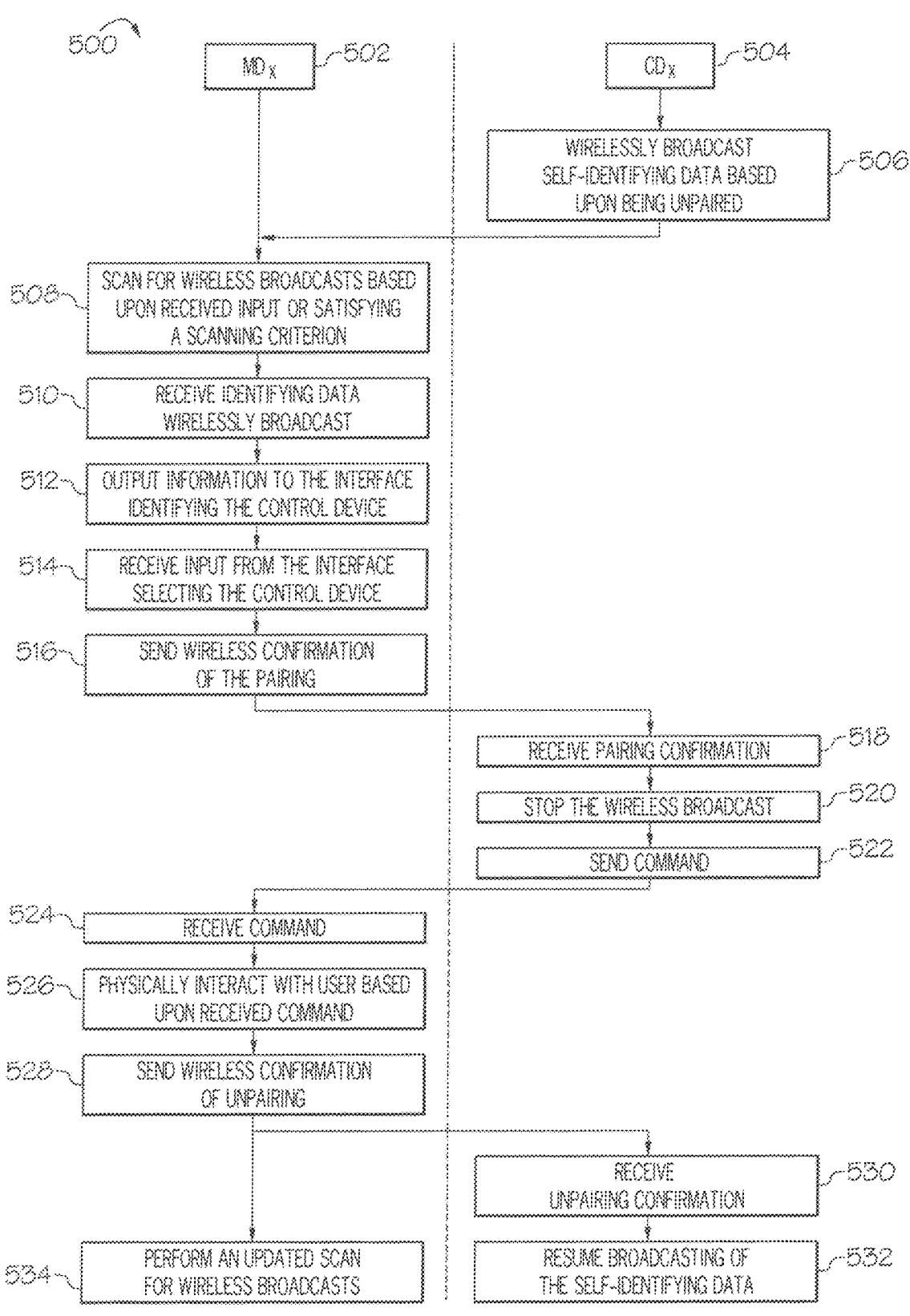
FIG. 5 depicts a flow diagram of an illustrative method for pairing a medical device and a control device using a wireless channel, according to one or more embodiments shown and described herein.

FIG. 5 depicts a flow diagram of an illustrative method
500 for pairing a medical device and a control device using
a wireless channel, according to one or more embodiments
of the present disclosure. Referring to FIG. 5, a medical
device $MD_X$ 502 may identify and pair with a control device
$CD_X$ 504, wherein the dashed vertical line in the center of the
flow diagram demarcates the respective operations of the
medical device $MD_X$ 502 and the control device $CD_X$ 504. At
block 506, the $CD_X$ may be unpaired and wirelessly broad-
cast self-identifying data, which may include a device name
and/or manufacturer-specific data (manufacturer, brand,
model, device, type, and the like). At block 508, the $MD_X$
may scan for wireless broadcasts based upon receiving input
(such as a user pressing a button on $MD_X$ or a button within
the medical device interface) or satisfying a scanning crite-
rion. For example, $MD_X$ may be a bed, in which setting its
brakes or being plugged into a wall for power may auto-
matically cause $MD_X$ to scan for control devices. Setting the
brakes or being plugged into the wall may be criteria that
indicate, for example, that $MD_X$ has reached its intended
destination (such as a particular room or partition within a
room) and scanning is now appropriate. In this way, $MD_X$
can conserve power by avoiding unnecessary scanning until
a destination has been reached.

At block 510, the medical device $MD_X$ may receive the
identifying data wirelessly broadcast from $CD_X$. Although
the wireless broadcast from $CD_X$ in block 506 is depicted as
intersecting within the flowchart prior to the scanning by
$MD_X$ at block 508, the wireless broadcast in block 506 may
intersect at any point up and/or including reception of the
$CD_X$ at block 510. At block 512, the medical device $MD_X$
may output information to the interface (e.g., FIG. 1C)
identifying the control device $CD_X$, in which the manufac-
turer-specific data may be filtered (e.g., handheld control
devices from a specific manufacturer may be displayed for
selection on the interface). At block 514, the medical device $MD_X$ may receive input at the interface selecting the control device. For example, a user may touch a screen selecting $CD_X$ from among other eligible control devices. At block 516, the medical device $MD_X$ may send wireless confirmation of the pairing to the control device $CD_X$. In this aspect, the medical device interface may add the medical device $MD_X$ to the list of selectable medical devices. At block 518, the control device $CD_X$ may receive pairing confirmation. In some aspects, the control device $CD_X$, may provide an indication of pairing/unpairing events, such as the indicator 232 in FIG. 2A, which may be a light such as an LED. At block 520, the control device $CD_X$ may stop its wireless broadcast due to being paired with a medical device $MD_X$. At block 522, the control device $CD_X$ may send one or more commands to the medical device $MD_X$. At block 524, the medical device $MD_X$ may receive the one or more commands from the control device $CD_X$. At block 526, based on the received command(s), the medical device $MD_X$ may physically interact with a user. As used herein, physical interaction with a user may include, by way of non-limiting examples, taking diagnostics or measurements (size/proportions, weight, temperature, heartrate, glucose, blood pressure, brainwaves, biorhythms, and the like) of a user, introducing or removing any suitable substance from any part of a user, diagnosing and/or alleviating/treating any disease or other ailment of a user, and/or assisting with the support, mobility, positioning, restraint, and/or comfort of the user.

At block 528, the medical device $MD_X$ may send wireless confirmation of unpairing, which may be accomplished via the medical device interface. This may be, for example, when the medical device $MD_X$ (a bed in this non-limiting example) is being moved to another room. At block 530, the control device $CD_X$ may receive subsequent confirmation of the unpairing. In some aspects, this may entail a visual, audio, or other indication associated with the control device $CD_X$, such as the indicator 232 in FIG. 2A. At block 532, the control device $CD_X$ may resume broadcasting self-identifying data in order to become paired with another medical device, such as a different bed that may be wheeled into the room in which $CD_X$ resides. At block 534, the medical device $MD_X$ may perform an updated scan for wireless broadcasts. This may be done, for example, when the medical device $MD_X$ has been wheeled into another room such that the brakes are engaged and/or the medical device $MD_X$ is plugged into the wall.

Figure 6:
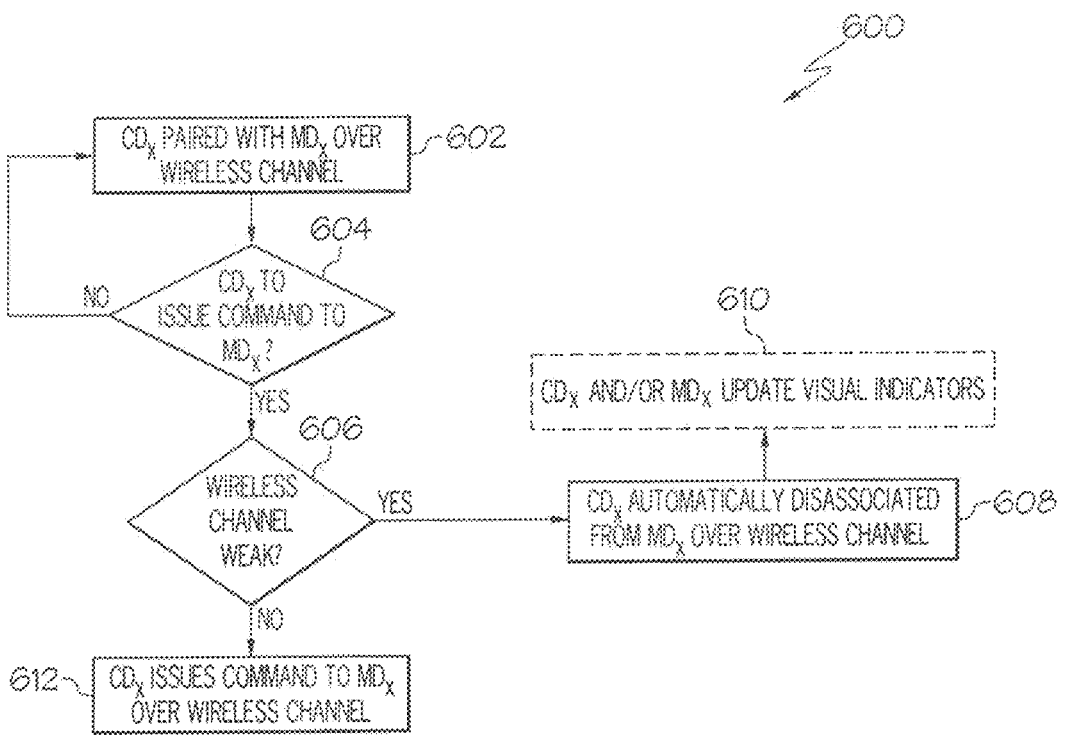
FIG. 6 depicts a flow diagram of an illustrative method for a control device to issue commands or control inputs to a paired medical device, according to one or more embodiments shown and described herein.

FIG. 6 depicts a flow diagram of an illustrative method 600 for a control device to issue commands or control inputs to a paired medical device, according to one or more embodiments of the present disclosure. According to various aspects, method 600 may be utilized for all control functions or only certain functions (e.g., actuating a motor, turning on a pump, and/or the like). Referring to FIG. 6, at block 602, a control device $CD_X$ may be paired with a medical device $MD_X$ over its wireless communication channel, as described herein. At decision block 604, the control device $CD_X$ may be configured to determine (e.g., based on inputs received via user interface controls 246 of FIG. 2A) whether a command or control input is to be issued or transmitted to the medical device $MD_X$. If it is determined that a command or control input is not to be issued or transmitted to $MD_X$, the control device $CD_X$ may remain paired with the medical device identifier $MD_X$ID over its wireless communication channel at block 602. If it is determined that a command or control input is to be issued or transmitted to the medical device $MD_X$, the control device $CD_X$ may be configured to determine whether the wireless communication channel is weak (e.g., below a predetermined threshold wireless signal strength) at decision block 606.

If it is determined that the wireless communication channel is weak, the control device $CD_X$ may be configured to automatically disassociate from the medical device $MD_X$ over the wireless communication channel at block 608. At block 610 (shown in phantom as an optional operation), the control device $CD_X$ may be configured to update its visual indicator to reflect the disassociation (e.g., LED off). If it is determined that the wireless communication channel is not weak, the control device $CD_X$ may be configured to, at block 620, issue the command or control input to the medical device $MD_X$ over its wireless communication channel. According to such aspects, if a medical device $MD_X$ is moved to an out-of-range location (e.g., no longer within the wireless range of the control device $CD_X$), then the control device $CD_X$ may be unable to issue a command or control input to the medical device $MD_X$, despite being otherwise able to over a strong wireless communication channel.

According to another embodiment, referring back to FIGS. 2A-2B, the control device 200 may include a location system 234 and the medical device 250 may include a location system 284. In such aspects, the medical device 250 and/or the control device 200 may be configured to further transmit their respective location information (e.g., MD LOC, CD LOC) with their respective identifiers (e.g., MD ID, CD ID) as described herein. In such aspects, the control device 200 may be configured to compare a received MD LOC (from the medical device) with its CD LOC as part of its process of pairing with a medical device. In some aspects, an initial range (e.g., about 2 m to about 5 m radius) may be used for initial pairing and a control range (e.g., average size of room) may be used for disassociation. In further aspects, the control device 200 may be configured to adjust/correct its CD LOC as well as the received MD LOC using a medical facility location MF LOC location beacon with known coordinates. Likewise, the medical device 250 may be configured to adjust/correct its MD LOC using a medical facility location MF LOC location beacon with known coordinates. According to various embodiments, such aspects may be used to further confirm the other identification methods as described herein. According to the various embodiments described herein, each wireless communication channel (e.g., Bluetooth channel) may be configured as a single-path communication channel or a dual-path communication channel.

It should be appreciated that while elements are described as optional, this is only with respect to one or more illustrative embodiments, such as program instructions stored in 206 FIG. 2A and 256 FIG. 2B, as well as the features depicted in 234 FIG. 2A, 284 FIG. 2B, and 610 FIG. 6. That is, these elements may be required in other embodiments. In addition, the depiction of these elements as optional does not imply that the processes described with respect to other elements in the respective figures are required.

It should now be understood that the systems and methods described herein are suitable for pairing a medical device and a control device using a wireless link (e.g., Bluetooth channel). In particular, the systems and methods described herein identify a configurable, pairable wireless connection (e.g. Bluetooth channel) to be used to execute control actions for a medical device (e.g., a portable medical bed) to ensure that the control inputs are coming from a control device (e.g., a tethered hand control unit, a wireless hand control unit, a wall-mounted control unit, a sling bar control unit, a coupling control unit, and/or the like) located in the same room as the medical device. Such systems and methods ensure that the control inputs coming from the control device are only directed to a medical device based upon user input received at the medical device that selects for pairing and/or control of the medical device.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A method for assisted medical device wireless pairing with a control device, the method comprising:

scanning, at the medical device, for wireless broadcasts based upon received input or satisfying a scanning criterion;

receiving, based upon the scan, identifying data wirelessly broadcast from a plurality of control devices;

outputting, to an interface at the medical device, information identifying the plurality of control devices, wherein:

the identifying data received from the plurality of control devices is presented on the interface according to a filtering criterion and a sorting criterion, and the sorting criterion comprises location information within the identifying data or respective signal strengths of each wireless broadcast;

receiving input from the interface selecting one of the plurality of control devices;

sending wireless confirmation of pairing to the selected control device;

receiving a command from the control device;

physically interacting with a user based upon the command received from the control device;

subsequently sending wireless confirmation of unpairing to the control device; and performing an updated scan for wireless broadcasts in response to the unpairing, based upon received input or satisfying the scanning criterion.

2. The method of claim 1, wherein the medical device comprises a medical bed, a pump, a rail-mounted lift, or a computer.

3. The method of claim 1, wherein the scanning criterion is based upon the medical device being plugged in or having brakes engaged.

4. The method of claim 1, wherein the filtering criterion comprises a device manufacturer, a device type, or a device model.

5. A pairable medical device, comprising:

a communication system configured to communicate via a communication channel;

an interface;

a processor; and a memory storing program instructions that, when executed by the processor, cause the processor to:

scan for wireless broadcasts based upon received input or satisfying a scanning criterion;

receive, based upon the scan, identifying data wirelessly broadcast from a plurality of control devices;

output, to the interface, information identifying the plurality of control devices, wherein:

the identifying data received from the plurality of control devices is presented on the interface according to a filtering criterion and a sorting criterion, and the sorting criterion comprises location information within the identifying data or respective signal strengths of each wireless broadcast;

receive input from the interface selecting one of the plurality of control devices;

send wireless confirmation of pairing to the selected control device;

receive a command from the control device;

physically interact with a user based upon the command received from the control device;

subsequently send wireless confirmation of unpairing to the control device; and perform an updated scan for wireless broadcasts in response to the unpairing, based upon received input or satisfying the scanning criterion.

6. The pairable medical device of claim 5, wherein the pairable medical device comprises a medical bed, a pump, a rail-mounted lift, or a computer.

7. The pairable medical device of claim 5, wherein the scanning criterion is based upon the pairable medical device being plugged in or having brakes engaged.

8. The pairable medical device of claim 5, wherein the filtering criterion comprises a device manufacturer, a device type, or a device model.

9. A non-transitory, processor-readable storage medium comprising instructions that, when executed by at least one processor, cause the at least one processor to perform one or more operations comprising:

scanning, at a medical device, for wireless broadcasts based upon received input or satisfying a scanning criterion;

receiving, based upon the scan, identifying data wirelessly broadcast from a plurality of control devices;

outputting, to an interface at the medical device, information identifying the plurality of control devices;

receiving input from the interface selecting one of the plurality of control devices;

sending a wireless confirmation of pairing to the selected control device;

receiving a command from the control device;

physically interacting with a user based upon the command received from the control device;

subsequently sending wireless confirmation of unpairing to the selected control device; and performing an updated scan for wireless broadcasts in response to the unpairing, based upon received input or satisfying the scanning criterion, wherein:

the identifying data received from the plurality of control devices is presented on the interface according to a filtering criterion and a sorting criterion, and the sorting criterion comprises location information within the identifying data or respective signal strengths of each wireless broadcast.

10. The non-transitory, processor-readable storage medium of claim 9, wherein the scanning criterion is based upon the medical device being plugged in or having brakes engaged.

* * * * *